(12) United States Patent
Shalon et al.

(10) Patent No.: US 11,629,079 B2
(45) Date of Patent: Apr. 18, 2023

(54) POOL AND SPA WATER QUALITY CONTROL SYSTEM AND METHOD

(71) Applicant: WATERGURU INC., Palo Alto, CA (US)

(72) Inventors: Tadmor Shalon, Palo Alto, CA (US); Richard A. Falk, San Rafael, CA (US)

(73) Assignee: WaterGuru Inc., Palo Alto, CA (US)

( * ) Notice: Subject to any disclaimer, the term of this patent is extended or adjusted under 35 U.S.C. 154(b) by 419 days.

(21) Appl. No.: 16/771,834

(22) PCT Filed: Dec. 18, 2018

(86) PCT No.: PCT/US2018/066167
§ 371 (c)(1),
(2) Date: Jun. 11, 2020

(87) PCT Pub. No.: WO2019/126127
PCT Pub. Date: Jun. 27, 2019

(65) Prior Publication Data
US 2021/0188672 A1   Jun. 24, 2021

Related U.S. Application Data

(60) Provisional application No. 62/607,243, filed on Dec. 18, 2017.

(51) Int. Cl.
*C02F 1/68* (2023.01)
*E04H 4/12* (2006.01)
(Continued)

(52) U.S. Cl.
CPC .............. *C02F 1/687* (2013.01); *C02F 1/686* (2013.01); *E04H 4/1272* (2013.01);
(Continued)

(58) Field of Classification Search
None
See application file for complete search history.

(56) References Cited

U.S. PATENT DOCUMENTS 2,758,710 A   8/1956 Arens
2,889,958 A   6/1959 Ekenstam et al.
(Continued)

FOREIGN PATENT DOCUMENTS

DE   3932400 A1   4/1991
JP   H05212387 A   8/1993
(Continued)

OTHER PUBLICATIONS

Blue I Water Technologies: Prizma; (http://www.blueitechnologies.com/products/prizma/); product page; 1 page; Accessed from the WayBackMachine on Jan. 19, 2018.
(Continued)

*Primary Examiner* — Richard C Gurtowski
(74) *Attorney, Agent, or Firm* — Shay Glenn LLP

(57) ABSTRACT

A water quality management system for a water installation containing water. In some embodiments, the system has a water quality measurement module adapted to monitor the water quality of the water in the water installation and to send water quality information to a controller; and a chemical dispensing module adapted to dispense at least one chemical directly into the water installation in response to signals from the controller based on a water quality measurement by the water quality measurement module, the chemical dispensing module comprising a reservoir adapted to contain the at least one chemical, a movable dispenser adapted and configured to advance a fixed quantity of the chemical out of the reservoir and into the water of the water installation in response to signals from the controller.

20 Claims, 14 Drawing Sheets

(51) Int. Cl.
  *G01N 21/78* (2006.01)
  *G01N 33/18* (2006.01)
  *C02F 103/42* (2006.01)

(52) U.S. Cl.
  CPC ........... *E04H 4/1281* (2013.01); *G01N 21/78* (2013.01); *G01N 33/18* (2013.01); *C02F 2103/42* (2013.01); *C02F 2209/005* (2013.01); *C02F 2209/02* (2013.01); *C02F 2209/06* (2013.01); *C02F 2209/40* (2013.01); *C02F 2303/04* (2013.01)

(56) References Cited

U.S. PATENT DOCUMENTS

| | | | |
|---|---|---|---|
| 3,638,833 A | 2/1972 | Lucas | |
| D233,887 S | 12/1974 | Bower et al. | |
| 4,056,470 A | 11/1977 | Carpenter | |
| 4,129,230 A | 12/1978 | Billett et al. | |
| 4,389,325 A | 6/1983 | Eng et al. | |
| D273,977 S | 5/1984 | Burrows | |
| 4,552,605 A | 11/1985 | Itoh et al. | |
| 4,769,137 A | 9/1988 | Powell, Jr. | |
| 4,780,197 A * | 10/1988 | Schuman | B01D 37/025 |
| | | | 210/136 |
| 4,825,528 A | 5/1989 | Nicholson et al. | |
| D307,460 S | 4/1990 | Bradford et al. | |
| 4,917,868 A | 4/1990 | Alexander et al. | |
| 5,019,250 A | 5/1991 | Lorenzen | |
| D358,868 S | 5/1995 | Hembree et al. | |
| 5,476,116 A | 12/1995 | Price et al. | |
| 5,614,528 A | 3/1997 | Jones et al. | |
| 5,662,795 A | 9/1997 | Pickens et al. | |
| 5,804,080 A | 9/1998 | Klingenberger | |
| 5,851,406 A | 12/1998 | Jones et al. | |
| 5,985,155 A | 11/1999 | Maitland | |
| 6,113,858 A | 9/2000 | Tang et al. | |
| 6,200,487 B1 | 3/2001 | Denkewicz et al. | |
| 6,238,553 B1 | 5/2001 | Lin | |
| 6,343,697 B1 | 2/2002 | Hausdorf et al. | |
| 6,387,251 B1 | 5/2002 | Marsiglietti et al. | |
| 6,567,166 B2 | 5/2003 | Ottens et al. | |
| 6,583,880 B2 | 6/2003 | Berstis | |
| 6,894,778 B2 | 5/2005 | Palumbo et al. | |
| D535,352 S | 1/2007 | Verdon | |
| 7,292,898 B2 | 11/2007 | Clark et al. | |
| 7,409,853 B2 | 8/2008 | Biberger | |
| D578,179 S | 10/2008 | Verdon | |
| 7,469,519 B2 | 12/2008 | Barthel et al. | |
| 7,544,289 B2 | 6/2009 | Straka et al. | |
| 7,745,517 B2 | 6/2010 | Vicari et al. | |
| D623,719 S | 9/2010 | Lees | |
| 8,007,664 B2 | 8/2011 | Reed et al. | |
| 8,133,398 B2 | 3/2012 | King et al. | |
| 8,197,755 B2 | 6/2012 | Tsur | |
| 8,309,509 B2 | 11/2012 | Bartelme et al. | |
| 8,345,248 B2 | 1/2013 | Hong et al. | |
| 8,404,117 B1 | 3/2013 | Steinbrueck et al. | |
| D687,512 S | 8/2013 | Cullimore | |
| D692,524 S | 10/2013 | Ziser | |
| 8,797,523 B2 | 8/2014 | Clark | |
| 8,968,660 B2 | 3/2015 | Davis et al. | |
| D730,484 S | 5/2015 | Kim | |
| 9,034,193 B2 | 5/2015 | Shalon et al. | |
| D742,997 S | 11/2015 | Sgroi | |
| D781,733 S | 3/2017 | Fernandes | |
| D795,994 S | 8/2017 | Malone et al. | |
| D807,985 S | 1/2018 | Shalon et al. | |
| 10,604,954 B2 | 3/2020 | Shalon et al. | |
| 2001/0044153 A1 | 11/2001 | Gangon et al. | |
| 2001/0045380 A1 | 11/2001 | Khan | |
| 2002/0056689 A1 | 5/2002 | Shim et al. | |
| 2004/0055969 A1 | 3/2004 | Barnes | |
| 2005/0139530 A1 | 6/2005 | Heiss | |
| 2006/0110292 A1 | 5/2006 | Deverse et al. | |
| 2007/0039898 A1 | 2/2007 | Dee | |
| 2007/0094817 A1 | 5/2007 | Stoltz et al. | |
| 2007/0138109 A1 | 6/2007 | Tufano et al. | |
| 2008/0008848 A1 | 1/2008 | Dick et al. | |
| 2008/0021685 A1 | 1/2008 | Emery et al. | |
| 2008/0094235 A1 | 4/2008 | Brochu et al. | |
| 2008/0311898 A1 | 12/2008 | Benco et al. | |
| 2009/0218296 A1 | 9/2009 | King et al. | |
| 2011/0125415 A1 * | 5/2011 | Mitsuyama | G01N 35/00603 |
| | | | 422/82.05 |
| 2011/0139727 A1 | 6/2011 | Hui | |
| 2011/0253638 A1 | 10/2011 | Easland et al. | |
| 2012/0187029 A1 | 7/2012 | Lauro et al. | |
| 2013/0168327 A1 | 7/2013 | Clark | |
| 2013/0273599 A1 | 10/2013 | Robitaille et al. | |
| 2014/0259612 A1 | 9/2014 | Bauckman et al. | |
| 2014/0299526 A1 | 10/2014 | Mastio | |
| 2015/0143785 A1 | 5/2015 | Sun | |
| 2015/0218835 A1 | 8/2015 | Shalon | |
| 2016/0259348 A1 | 9/2016 | Lewis et al. | |
| 2017/0092096 A1 | 3/2017 | Fernandes et al. | |
| 2020/0217098 A1 | 7/2020 | Shalon et al. | |
| 2022/0003014 A1 | 1/2022 | Shalon et al. | |

FOREIGN PATENT DOCUMENTS

| | | |
|---|---|---|
| JP | 3089916 B2 | 7/2000 |
| WO | WO20160176169 * | 11/2016 |
| WO | WO2017/024199 A1 | 2/2017 |

OTHER PUBLICATIONS

Bullock; Disinfection of swimming pool water; PhD Thesis; Chapter 5 Material and Methods; pp. 60-79; Cranfield University; Oct. 2003.

OnBalance; The role of CO2 in pool water; 5 pages; Jan. 2006; (retrieved from the internet: http://www.anotherperfectpoolnews.com/wp-content/uploa:ds/Tech_Talk/onbalance_ks_co2inwater.pdf).

Wojtowicz; Chemistry of nitrogen compounds in swimming pool water; JSPSI; 4(1); pp. 30-40; Jan. 2004.

* cited by examiner

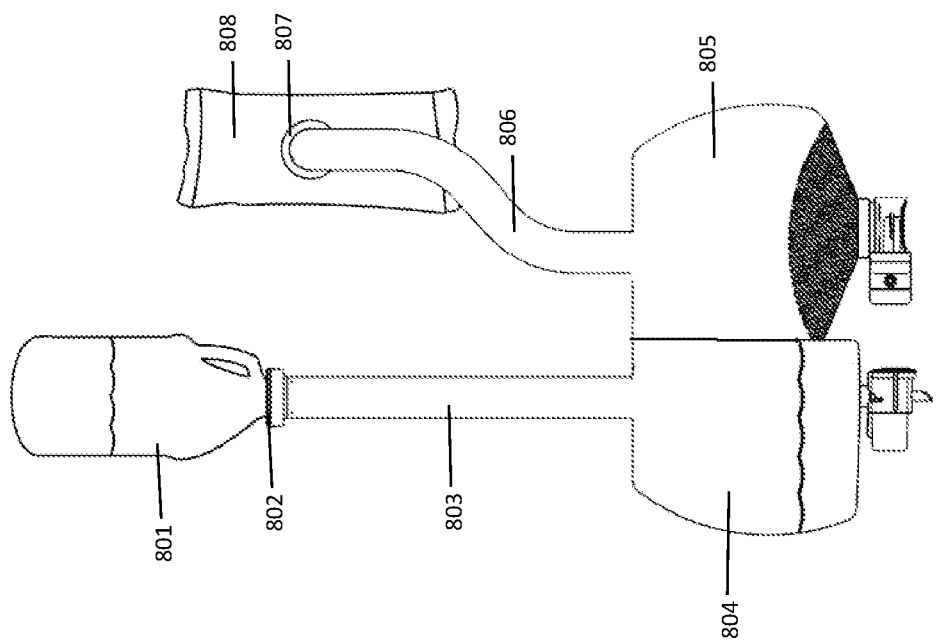

POOL AND SPA WATER QUALITY CONTROL SYSTEM AND METHOD

CROSS REFERENCE TO RELATED APPLICATIONS

This application claims the benefit of U.S. Application No. 62/607,243, filed Dec. 18, 2017, the disclosure of which is herein incorporated by reference in its entirety.

INCORPORATION BY REFERENCE

All publications and patent applications mentioned in this specification are incorporated herein by reference in their entirety to the same extent as if each individual publication or patent application was specifically and individually indicated to be incorporated by reference.

FIELD

The present invention relates to an affordable, modular, and convenient system for homeowners to deploy in their pools or spas in order to optimally maintain the water quality in a safe and responsible way while minimizing use of chemicals and energy.

BACKGROUND

Nearly 15 million US homeowners struggle to optimally control the quality of the water in their pools. (As used herein, "pools" includes spas.) The water is affected by environmental factors such as sunlight, wind, pollen, debris, rain and human factors such as skin and fecal bacteria, sweat and urine. Most homeowners or their hired pool service make adjustments on a weekly basis at best. In order to deal with changing conditions, most users overdose their pools with circulating disinfectants, resulting in harsh water that attacks skin, hair and bathing suits, and often requiring additional chemicals to maintain pH. Water chemistry parameters are mutually dependent where free chlorine ("FC") requires a narrow pH range in order to effectively oxidize organic matter and purify the water. If not enough effective disinfectant is present, nutrients in the pool can cause an algae bloom requiring further expensive chemicals and environmentally damaging water change often in excess of 15,000 gallons. This results in over $2.6 billion spent each year in the US by consumers on pool chemicals such as disinfectants, water balance adjusters (for pH, total alkalinity, calcium hardness, and cyanuric acid), algaecides, clarifiers, flocculants, and enzymes which need to be manually administered to pools. Since the popularization of back yard pools in over 15% of all households, no automatic, easy to deploy, cost effective systems have been commercially available to address these needs.

Over 80% of pool and nearly 90% of spa owners in the US maintain their own pools and spas and are not able or willing to make significant investment in installing new equipment requiring plumbing or electrical connections.

Several partial solutions have been offered to the consumer. Manual colorimetric test strips exist that indicate the state of chemicals in the pool water, but those must be applied manually, read on multi-colored comparison charts, and translated to the correct balancing mixture of chemicals needed. It is difficult for the user to connect these weekly measurements and compute the dynamic trajectory of pool water and the required corrective action. This results in over or under correction both of which can be very expensive.

There exist some automation systems for the residential pool market (e.g., the Hayward Sense and Dispense® system). These systems are costly to install and costly to maintain. In addition, they require a disruption of existing plumbing. These systems control only for chlorine and pH and have oxidation-reduction potential (ORP) sensors with a sensitive platinum electrode and pH sensors with a sensitive glass bulb, both of which need regular maintenance for calibration and cleaning.

Balancing the pH, alkalinity, and calcium levels of the pool water requires additional measurements, calculations and manual administration of chemicals.

It should be further appreciated that all of the processes affecting pool water chemistry mentioned above are not linear, yet users routinely attempt to control them with step adjustments such as adding a fixed amount of chemicals, or changing the setting on a chlorine dispenser, pump timer, etc., subject to infrequent measurement, typically once per week at best. This approach inevitably results in suboptimal adjustments. The present invention describes a modular battery-operated system that may be easily deployed one module at a time to deal with the tedious aspects of pool maintenance and that relieves the user from these manual tasks by making repeated measurements and providing optimized dynamic dosing to keep pool water in ideal condition.

It should be further appreciated that pool service personnel currently use fixed schedules and routes resulting in either visiting pools on their route too frequently or too infrequently often involving considerable driving time and expense. The present invention automatically takes care of most maintenance issues, advises the service center of pool conditions and often proactively reports service issues before they become problems, thereby allowing pool service personnel to perform their work more efficiently by minimizing truck rolls and optimizing routing based on actual service need.

It should be further appreciated that any man-made body of water may require chemical monitoring and adjustment. Cooling towers have to be routinely maintained with sanitizer to avoid bacteria growth that can lead to Legionnaires' disease. In addition to cooling towers, hot tubs, fountains, koi ponds, containment ponds and other open or closed water systems could benefit from one or more of the modules described herein each of which is of low cost, requiring no complex calibration or cleaning, and all but one (the pump control module) are easily added to the pool by the pool owner without need for professional installation.

Colorimetric strips (e.g., Hach Aquachek®, ITS Sensate®, LaMotte Insta-TEST®) have been available for decades and are the most popular means for analyzing the key analytes in pool water such as FC, pH, alkalinity, and hardness. These pad strips must be manually dipped in the water and the color of the pads compared to a standard chart to read the analyte level. The pad strips must be kept in a sealed container so they do not degrade due to exposure to moisture in the form of liquid water or water vapor present in humid air.

Electronic probes for measuring pH and ORP (which is related to, but not a direct measurement of FC) have been available in commercial systems, but these probes are prone to degradation and calibration drift. While some of these systems simply provide open loop monitoring, others control the dispensing of chemicals based on monitored parameters, such as in U.S. Pat. No. 8,797,523.

Automated pool chemical sensing technology suffers from certain drawbacks. For example, systems have been proposed to sequentially expose pads to pool water as described in U.S. Pat. Nos. 6,113,858 and 8,197,755 or as demonstrated by the Blue I Water Technologies PRIZMA® system (http://www.blueitechnologies.com/products/prizma/), but they do not provide for a way to prevent moisture degradation to the analyte pads or the ability to keep them in the pool water prior to use.

In addition to water chemical monitoring, turbidity monitors have been used to control water circulation pumps in pools, such as described in US Publ. No. 2011/0253638. Circulating water pumps have also been controlled based on pool usage, as described in U.S. Pat. No. 5,804,080.

SUMMARY OF THE DISCLOSURE

One aspect of the invention provides a water quality management system for a water installation containing water, the system having a water quality measurement module adapted to monitor the water quality of the water in the water installation and to send water quality information to a controller; and a chemical dispensing module adapted to dispense at least one chemical directly into the water installation in response to signals from the controller based on a water quality measurement by the water quality measurement module, the chemical dispensing module comprising a reservoir adapted to contain the at least one chemical, a movable dispenser adapted and configured to advance a fixed quantity of the chemical out of the reservoir and into the water of the water installation in response to signals from the controller.

In some embodiments, the movable dispenser is an auger. The auger may be partially disposed in a tube extending to an exit port of the reservoir and partially disposed in the reservoir above the tube. The system may also optionally have a flexible seal extending from the tube, the flexible tube having an open configuration in which chemical is permitted to flow from the tube into the water installation and a closed configuration in which the flexible seal seals the exit port of the reservoir. In such embodiments, the system may also optionally have an actuator (such as, e.g., a pair of pinchers operated by a motor) moving the flexible seal from the open configuration to the closed configuration.

In some embodiments, the movable dispenser is a rotating scoop.

In any of these embodiments, the chemical may be a powdered chemical, the reservoir having a sloped bottom surface enabling the chemical to flow by gravity through the first port. In such embodiments, the slope may be between 20 degrees and 50 degrees from vertical.

Another aspect of the invention provides a water quality management system for a water installation containing water, the system having a water quality measurement module adapted to monitor water quality of the water in the water installation and to send water quality information to a controller; and a chemical dispensing module adapted to dispense at least one chemical directly into the water installation in response to signals from the controller based on a water quality measurement by the water quality measurement module, the chemical dispensing module having a reservoir adapted to contain the at least one chemical, a measurement chamber having a volume smaller than a volume of the reservoir, a first port between the reservoir and the measurement chamber having an open position and a closed position, a second port between the measurement chamber and the water installation having an open position and a closed position, the first port and the second port being controlled by the controller to not be open at the same time.

In some embodiments, the system also has a valve having a first state corresponding to the open position of the first port and the closed position of the second port and a second state corresponding to the closed position of the first port and the open position of the second port. In some embodiments, the valve is a rotary valve. The system may also have an optional a rotation stop configured to prevent more than one rotation of the valve.

In some embodiments, the chemical is gravity fed from the measurement chamber into the water installation when the second port is in the open position.

Some embodiments of the invention also have a rotatable scoop having an opening, the scoop having a first state corresponding to the open position of the first port and the closed position of the second port and a second state corresponding to the closed position of the first port and the open position of the second port. In some embodiments, the second port comprises a movable door. Some embodiments also have a stop configured to prevent continuous rotation of the scoop.

Some embodiments have a first sliding plate comprising an opening, the first sliding plate having a first state corresponding to the open position of the first port and a second state corresponding to the closed position of the first port and the open position of the second port; and a second sliding plate comprising an opening, the second sliding plate having a first state corresponding to the closed position of the first port and a second state corresponding to the open position of the first port and the open position of the second port.

Some embodiments of the invention also have a first valve adapted to open and close the first port and a second valve adapted to open and close the second port. In some such embodiments, the measurement chamber comprises a flexible tube that may be configured to deform when the second valve closes the second port to seal the measurement chamber.

In some embodiments, the chemical is a powdered chemical, the reservoir comprising a sloped bottom surface enabling the chemical to flow by gravity through the first port. The slope may be between 20 degrees and 50 degrees from vertical. Such embodiments may also have a vibrator adapted to vibrate the reservoir.

Yet another aspect of the invention provides a water quality management system for a water installation containing water, the system including a water quality measurement module adapted to monitor the water quality of the water in the water installation and to send water quality information to a controller; and a chemical dispensing module adapted to dispense at least one chemical directly into the water installation in response to signals from the controller based on a water quality measurement by the water quality measurement module, the chemical dispensing module comprising a dosing chamber; an inlet in fluid communication with the dosing chamber and adapted to fluidly connect to water from the water installation downstream of a high pressure outlet of a water installation circulation pump, an outlet in fluid communication with the dosing chamber and adapted to fluidly connect with a low pressure inlet of the water installation circulation pump, and a reservoir adapted to contain the at least one chemical, the reservoir having an outlet communicating with the dosing chamber.

In some embodiments, the water quality measurement module is in fluid communication with the dosing chamber. In some embodiments, the chemical dispensing module further comprises a float in the dosing chamber and a valve at the inlet controlled by the float. In some embodiments, the chemical dispensing module further comprises a valve at the outlet adapted to be operated when the circulation pump operates.

Still another aspect of the invention provides a water quality management system for a water installation containing water, the system having a water quality measurement module adapted to monitor the water quality of water flowing through a circulation system of the water installation and to send water quality information to a controller; a flow sensor adapted to sense a flow of water through the circulation system and to send flow information to the controller; and a chemical dispensing module adapted to dispense at least one chemical directly into water flowing through a circulation system of the water installation in response to signals from the controller based on a water quality measurement by the water quality measurement module and flow sensed by the flow sensor.

In some embodiments, the flow sensor comprises a heated element disposed to be in contact with water flowing through the circulation system and a temperature sensor adapted to sense a temperature of the heated element. In some embodiments, the flow sensor comprises a microphone. In some embodiments, the flow sensor comprises an accelerometer.

BRIEF DESCRIPTION OF THE DRAWINGS

FIG. 8 shows fill tubes connecting a liquid bottle and powder bag to their respective reservoirs of a chemical dispensing module of a water quality management system for a water installation according to embodiments of the invention.

DETAILED DESCRIPTION

Figure 1:
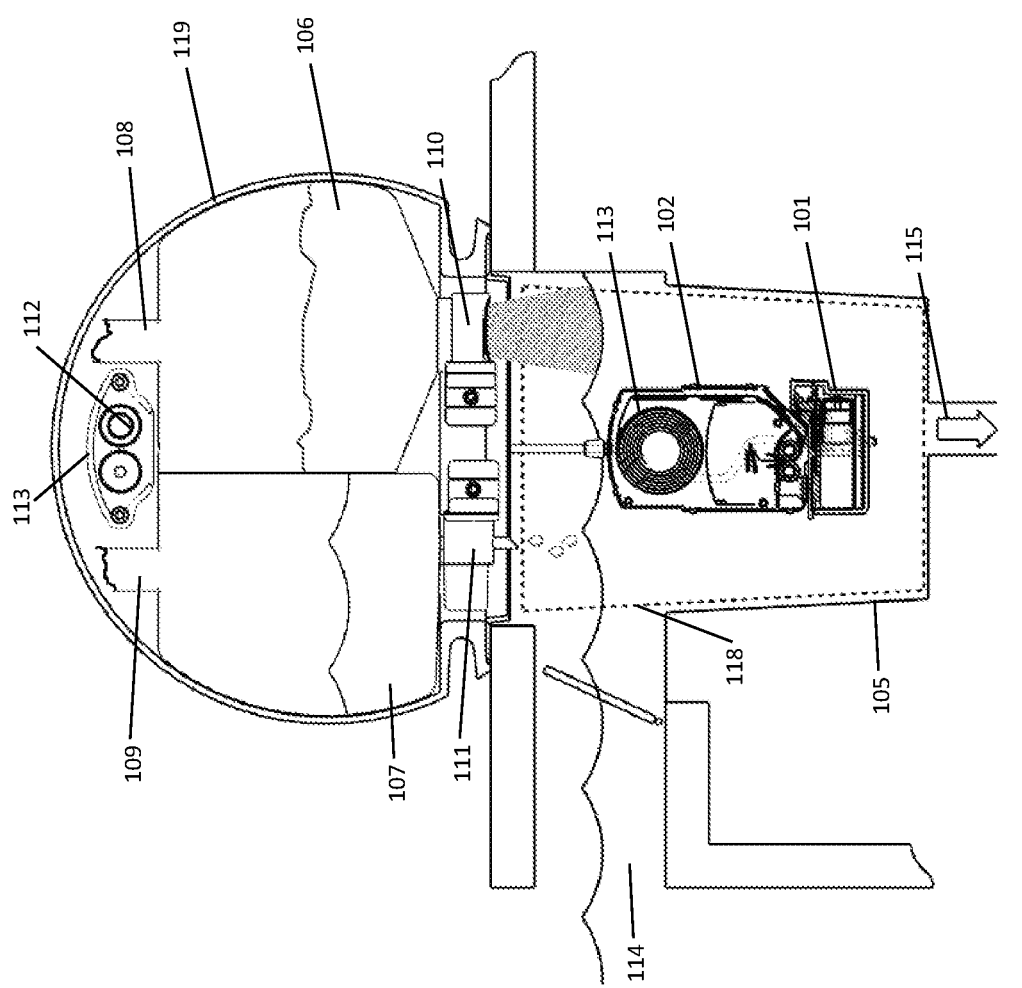
FIG. 1 shows a water quality management system for a water installation according to an embodiment of the invention installed on a pool skimmer.

The invention provides an integrated system for pool water maintenance whose components each may also be used separately. FIG. 1 shows one embodiment of this invention as a system 119 placed on a typical pool skimmer 105 with a leaf basket 118 that measures and treats pool water 114 as it is pumped through the skimmer to skimmer outlet port 115. The system includes a water chemistry measurement module 101 with a disposable cassette containing multiple colorimetric test pads 102 and mechanisms to expose each of these pads to water and read their color change. The test pads 102 may be, e.g., as described below or as described in U.S. Pat. No. 9,034,193. The system may include a chemical dispensing module having one or more reservoirs, for example, reservoir 106 for powder and reservoir 107 for liquid reagents, each with its own fill tube, 108 and 109, respectively, and dispenser, 110 and 111, respectively, each capable of dispensing a known volume of chemical from the reservoir to the pool water while ensuring that under no circumstance the content of the reservoir can be accidentally discharged into the water. This system can be powered by a battery 112, which can be optionally charged by a solar cell, and controlled by onboard electronics 113 capable of controlling all the motors and actuators and communicating via RF signals to outside devices or to a remote data storage and analysis system.

Figure 2:
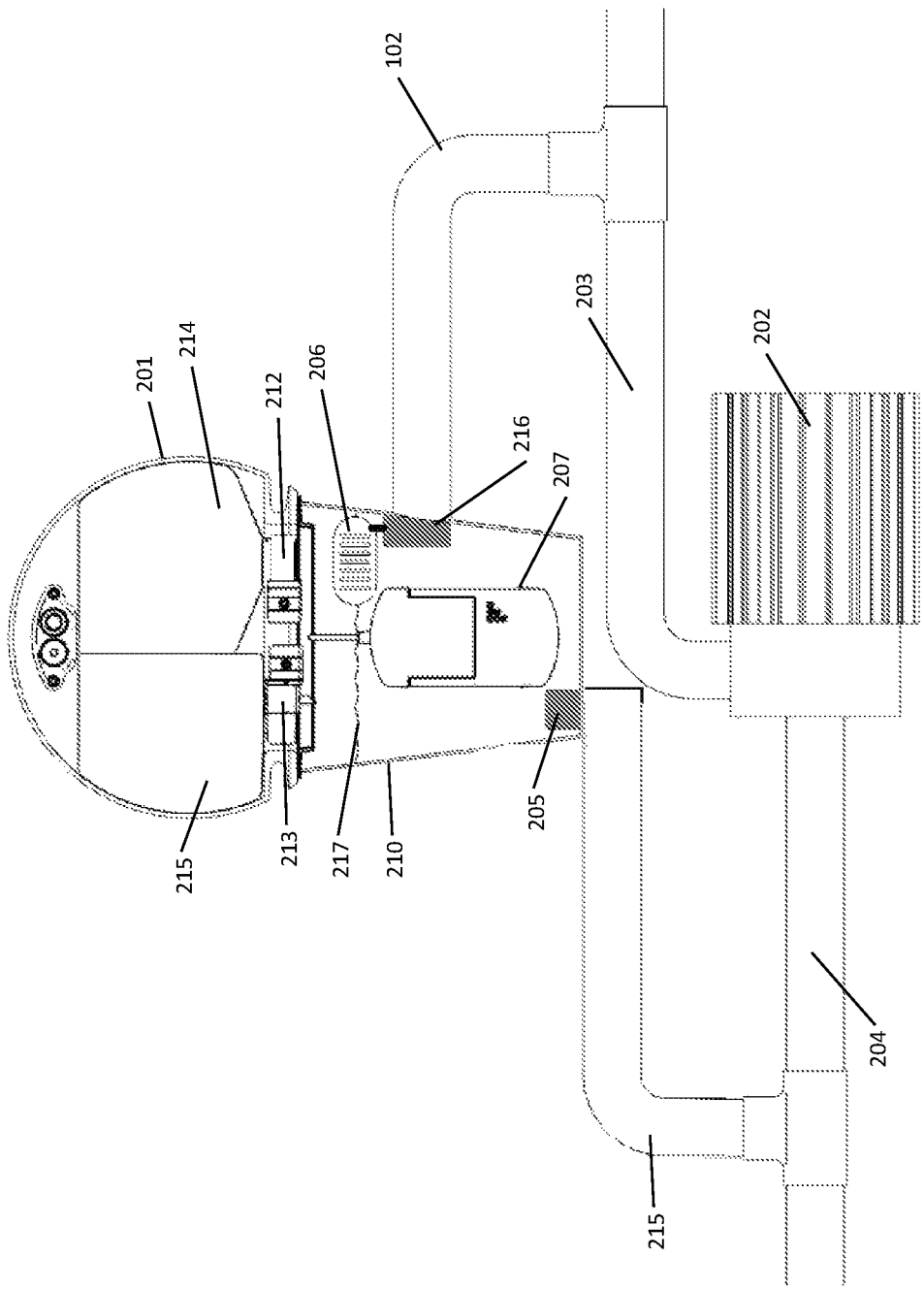
FIG. 2 shows a water quality management system for a water installation according to another embodiment of the invention installed on a pool low pressure injection station of the water installation.

This system 201 can also be deployed as shown in FIG. 2 on a pool equipment room low pressure injection station 210. The injection station extracts a portion of the water, for example 5-30%, from the high pressure outlet 203 of the pool's circulation pump 202 after the water passes through other pool equipment such as a filter or heater and returns the treated water back into the circulation pump's low-pressure input 204 via pipe 215. When the pump operates, an electronically controlled valve 205 is activated by the device, and a level sensing float 206 in the dosing chamber insures that the water leaving the dosing chamber through valve 205 is replenished via the float controlled valve 216 and to maintain the water level 217 in the injection station dosing chamber. The extracted water within the dosing chamber can be used for testing by the measurement module 207 and for receiving the chemicals dispensed from reservoirs 214 and 215 via dispensers 212 and 213, which are further mixed into the pool water via the circulation pump, thus keeping the testing and treatment water under normal atmospheric pressure, suitable for treatment by the system described in this disclosure.

It is well known that moisture and humidity interfere with the ability of colorimetric chemistry analysis pads to accurately test for the analyte for which they were designed. For example, samples of LaMotte free Chlorine measurement strips (LaMotte, Insta Test 3 Swimming pool Test Strips) were exposed to a high relative humidity environment at a temperature of 52 C for four days (equivalent to 16 days at pool temperature of 32 C in FL). Exposed strips and unexposed strips were tested per manufacturer's instructions using a calibrated 3 ppm free chlorine solution and measurements of the exposed strips measured 0 ppm (STD 0.14) and the of control strips were 2.9 ppm (STD 0.3). The pH pads were tested per manufacturer's instructions using a calibrated pH 8.0 solution and the measurements were 4.83 (STD 0.3) for the exposed strips and 8.11(STD 0.2) for the control strips. Other vendors' products tested similarly.

Figure 3A:
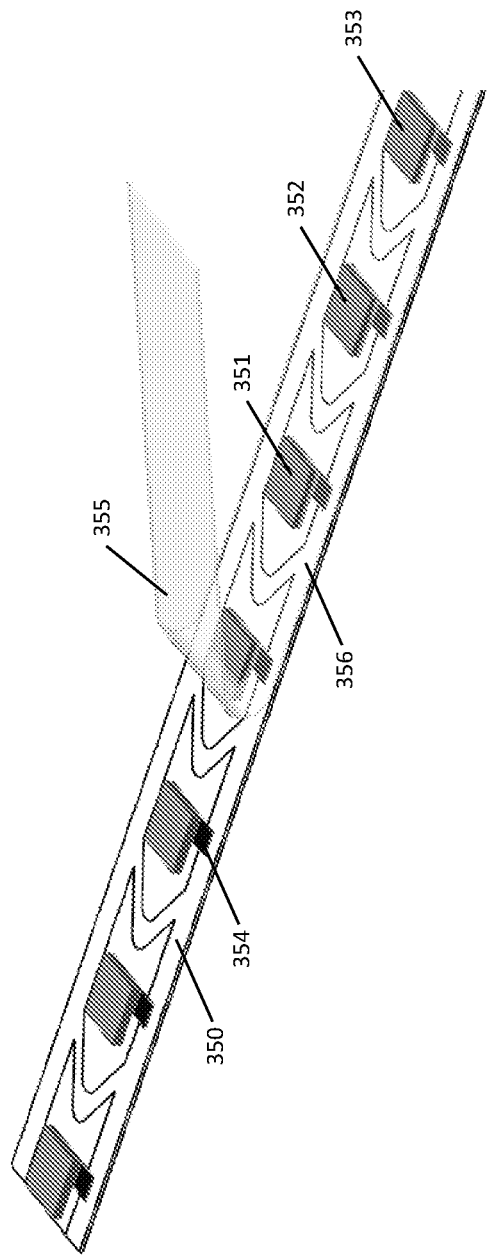
FIG. 3A shows a strip of colorimetric chemical measuring pads for use in a water quality measurement module of a water quality management system for a water installation according to embodiments of the invention.

In one aspect of this invention, as shown in FIG. 3A, the chemical detection pads 351, 352, and 353 are attached to a bottom film 350. The bottom film has optical alignment marks such as 354 that allow the system to align the pad under the optical system. A top film 355 is heat sealed to the bottom film 356 around each pad. The colorimetric pads can be made for several chemical analytes (LaMotte, Maryland MD), and can be sequenced in the strip during manufacturing. For example, pad 351 can be for free chlorine using TMB dye, 352 for pH using derivatized phenol red dye, and pad 353 can be a reference pad that does not change color when exposed to water in order to calibrate the colorimetric sensor. This pattern repeats or alternates as needed for a long strip of such pads.

The films 350 and 355 are made of transparent and sufficiently low water vapor transmission rate ("VTR") (e.g., Toppan® GLRD/2 film) with a suitable thermally sealed peel layer. For example, the film can be made of multiple layers such as PET layer for structural integrity, one or multiple aluminum or silicone oxide layers as a water vapor barrier, protective over coating, appropriate adhesive and a LDPE-PB peelable heat seal layer.

Alternatively, the films can be made of a non-transparent material such as a PET layer for structural integrity, a thin aluminum layer, an appropriate adhesive and a LDPE-PB peelable heat sealed layer. During operation as explained below, the film is pulled in opposite directions through two separate pinch rollers that are geared together or onto two separate wound-up rollers that are synchronized by the system such that one pad at a time can be exposed to the optical color analysis system.

Alternatively, in order to further reduce the ingress of vapor into the sealed pad through the seal layer between the top and bottom films, the film can utilize a non-peelable film and pass the film through blades that cut the top film and then pull it in such a way the cut film is deformed to allow the pad to be exposed to water.

Figure 3B:
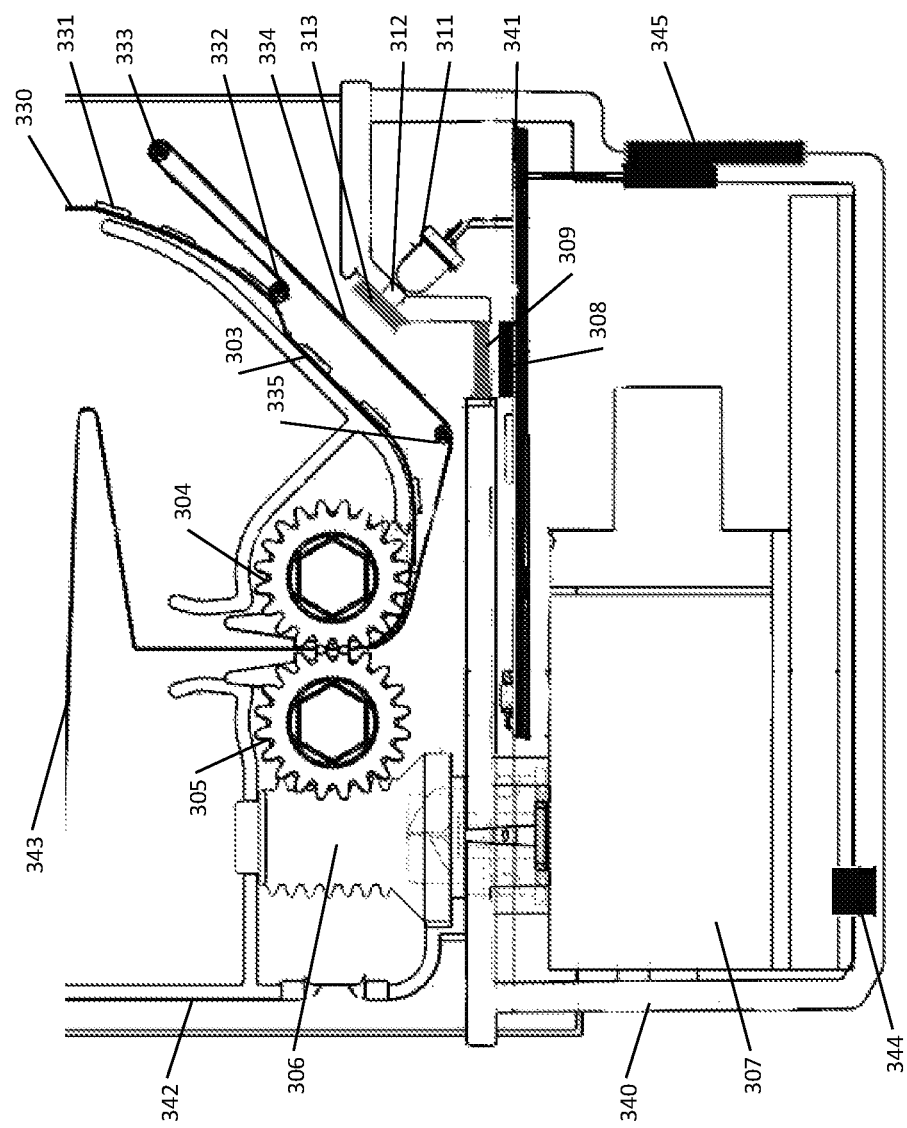
FIG. 3B shows a water quality measurement module of a water quality management system for a water installation according to embodiments of the invention.

A typical single drive system for use with the film shown in FIG. 3A is shown in FIG. 3B. It is submerged in water or a separate pump brings pool water and floods the measurement chamber. A water tight enclosure 340 contains the electronics 341, a gear motor 307, the optical components and sensors. The film cassette 342 contains a spool of film 113 shown in the cassette in FIG. 1 and pulls it through a set of pins, via pinch rollers 304 and 305 rotated by gear motor 307 and driven gear 306 to be opened one sealed pad cell at a time and to expose the pad 303 contained within to water under the optical color sensor. The film strip 330 containing sealed pads such as 331 is pulled via pin 332, and the top clear film 334 is pulled through pins 333 and 335 which keep it taught under the optical detector. The wet pads are pinched back into the film by rollers 304 and 305, and the spent film 343 is stored in the cassette. The mechanism is tilted 45 degrees so that any air bubbles from the pump or trapped in the film will float away from the measurement system.

The optical sensor consists of a colored light emitter 308, such as multi-colored LEDs or a filtered broad spectrum light source, transmitting light through window 309 that seals the system in enclosure 340. A photo detector 311 reads the reflected light intensity through a narrow tube 312 that acts as a spatial filter and limits its field of view to the pad and through window 313. The light source and detector are arranged to minimize reflections from the transparent films 334 and other surfaces as shown. In another configuration, a white light source can be used in position 308 in combination with a color mask or diffraction gratings with photo detectors in position 309. The film may also contain a registration mark next to each pad as shown before and a separate photo detector next to 311 to sense each mark and provide a signal to the control electronics so that it can accurately align the pad under the optical color detection system.

Over time the chemicals in the pad interact with those in water to change color attributes such as saturation, hue or intensity. However, the sensing chemical can also desorb from the pad or interact with other chemicals in the water (such as chlorine) and lose color parameters over time. Hence, the color detection system can read the pad color over time based on the chemistry of the pad and the water in order to optimize the measurement sensitivity.

This unit can be suspended or floated in the pool water, or alternatively water can be pumped from the pool the area where the pads can be submerged in water.

The device and method of this invention detects water flow in the skimmer of the pool before measurements are made in order to insure the measurements represent the average chemistry of the pool. The device and method of this invention also discharges the treatment chemicals in a manner that insures that the chemicals mix well with the pool water, that they do not reach too high a local concentration (such as a low pH when adding acid or a high level of chlorine) that can damage pool equipment, and that incompatible chemicals such as a strong acid and chlorine do not interact to create dangerous by products such as chlorine gas. It is also desired not to connect sensors and wires directly between this equipment and the pump due to the cost and possible hazard they represent. It is also desired not to have a mechanical moving sensor to sense water flow because debris in the pool can jam such a detector. In order to create a reliable flow sensor, an encapsulated microphone or accelerometer acting as a hydrophone 344 is suitably acoustically coupled to the water can sense the pump sound carried by the water and further process it via FFT and detect the acoustic spectrum signature of the pump.

In yet another aspect of this invention, a transistor's metal heat sink 345 or other device such as a resistor or diode capable of being electrically heated is exposed to the water. The transistor or other suitable temperature sensor is also used to read the temperature of the heat sink. The temperature of the heat sink is read, the transistor is heated by a known amount of energy electronically, e.g., 15 J, and the temperature is read again. Subsequent temperature measurements are made every 60 milliseconds. The peak temperature as well as temperature decay is proportional to the conductance of heat away from the heat sink by the water and can distinguish the flow of water which increases the rate of heat loss with water as well as to distinguish when the sensor is in air versus water.

Figure 4:
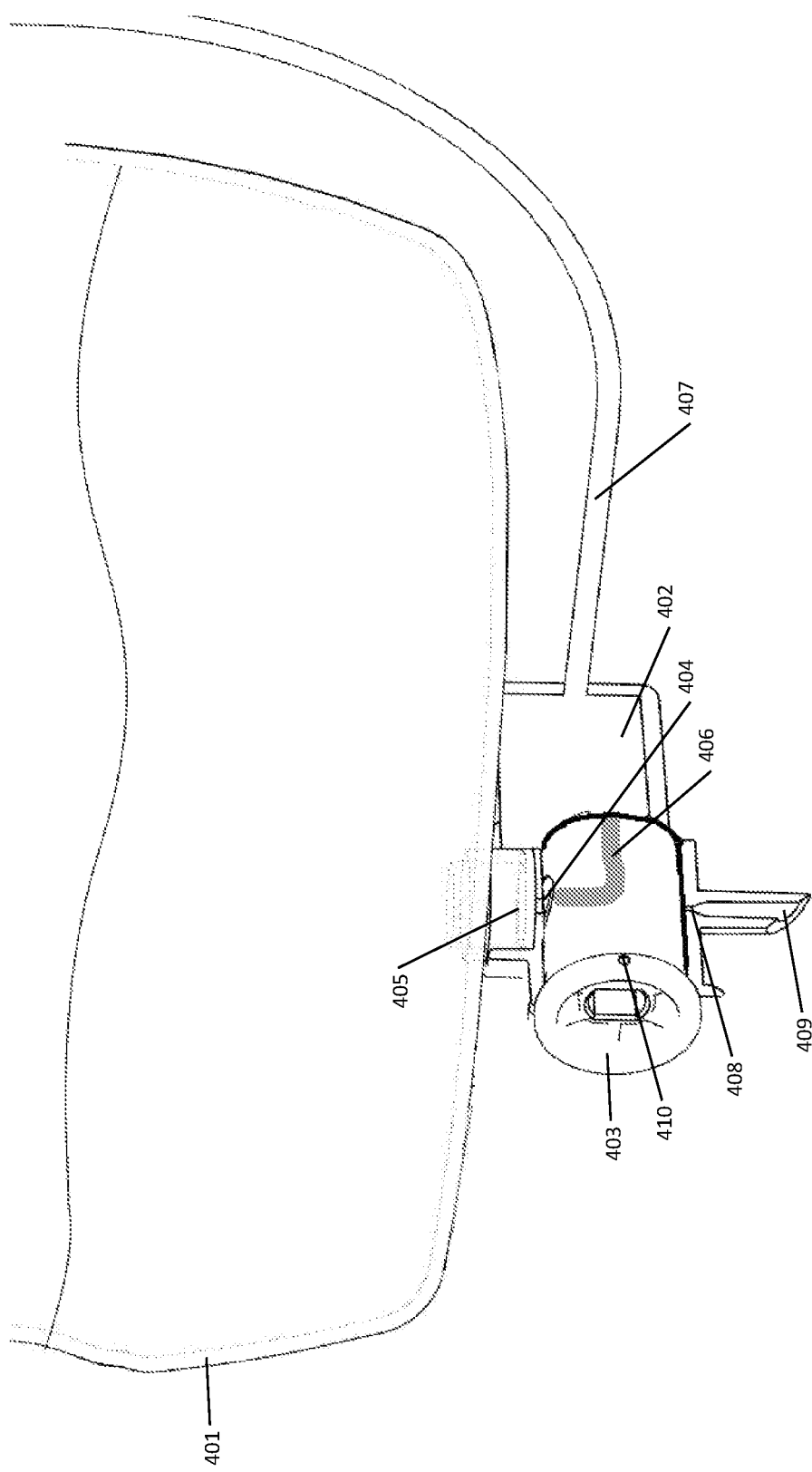
FIG. 4 shows a liquid reagent dispenser of a chemical dispensing module of a water quality management system for a water installation according to embodiments of the invention.

Another aspect of the invention is the safe dispensing of a liquid such as hydrochloric acid into the pool water in order to lower the pH. These concentrated chemicals must be dispensed slowly in order not to crash the pH, for example, less than 6 mL per minute into a 10 gpm water flow in a skimmer. FIG. 4 shows such a liquid dispenser with a chamber 402 that isolates the reservoir 401 from the pool water so that the contents of the reservoir 401 will not flow uncontrollably into the pool water. The holding chamber 402 has a volume of 30 mL and is filled via valve 403 when the valve opening 404 is rotated upward toward the reservoir's filtered outlet 405, enabling liquid to flow from the reservoir through opening 404 to fill the tank via channel 406. Air escapes via vent tube 407. When the system's water quality measurement module indicates that chemicals need to be added to the water, the system's controller actuates the motor to rotate the valve 180 degrees so that the valve opening 404 points downward. The holding chamber's content is then gravity fed through channel 406 to valve opening 404 through a small orifice 408 to control the drip rate into the pool water via nozzle 409. In order to insure safety, a rotational stop prevents the valve from rotating more than 350 degrees or more than one rotation in case the motor or control electronics fail, resulting in the motor's continuous rotation and dispensing of the all of the contents of the reservoir into the pool and endangering the users. Magnet 410 and respective Hall Effect sensor or other suitable sensing system allows the control electronics to precisely position the valve in the up or down position over respective orifices 405 and 408.

Figure 5:
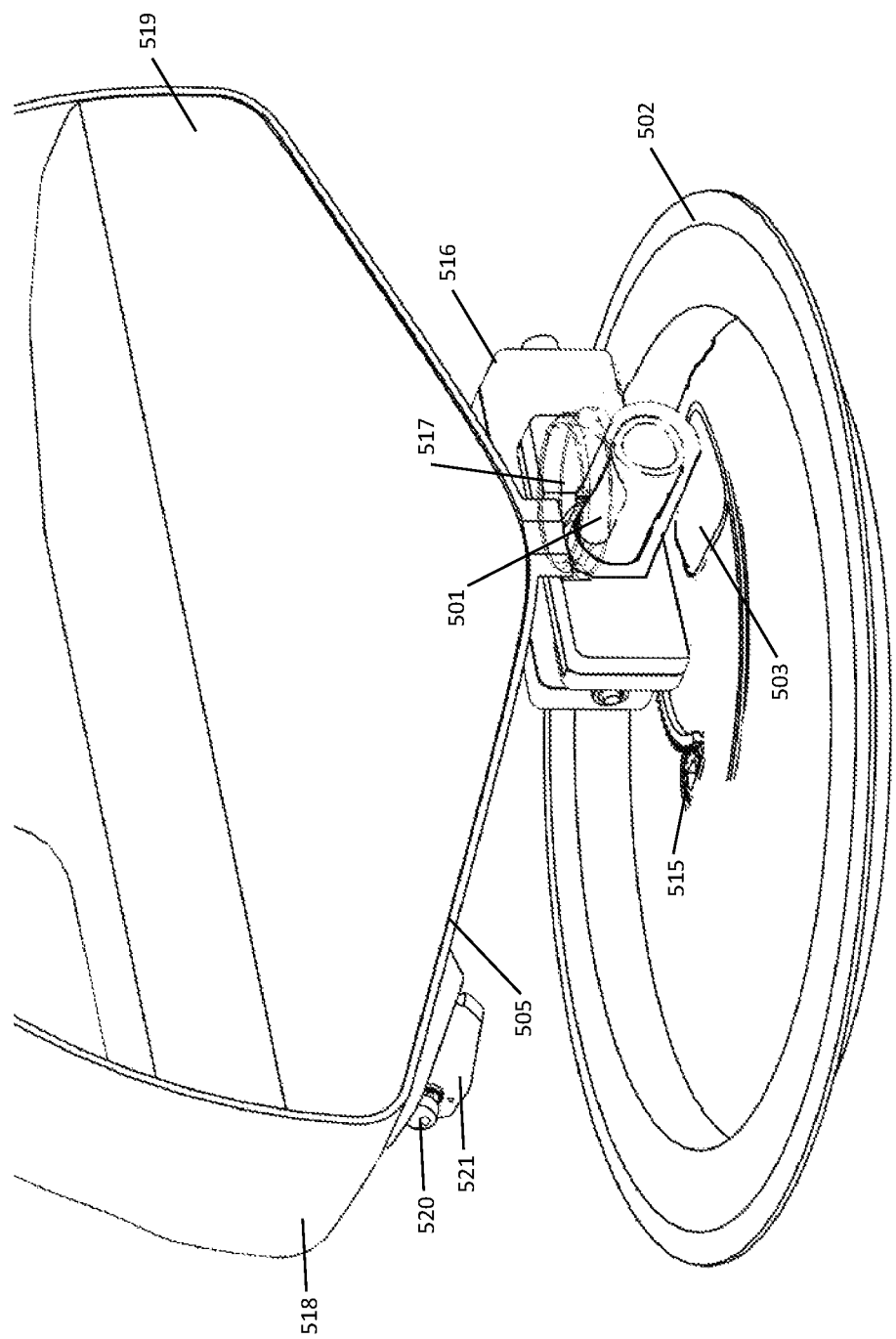
FIG. 5 shows a rotating scoop powder reagent dispenser of a chemical dispensing module of a water quality management system for a water installation according to embodiments of the invention.

In yet another aspect of this invention, hydroscopic powders or granules such as calcium hypochlorite are dispensed into the pool water to sanitize it. Hydroscopic powders readily absorb humidity and can clump and jam the dispenser. The fine particles present in the powder coat and cling to moving parts and can jam the dispenser. In one embodiment shown in FIG. 5, when the system's water quality measurement module indicates that chemicals need to be added to the water, the system's controller actuates a gear motor with magnetic positioning encoder 516 rotates a scoop 501 having an opening that fills with powder 519 from the reservoir 518 via a funnel opening at its bottom 517. The scoop 501 has a volume much smaller than the volume of reservoir 518, e.g., 5 mL. When the scoop is rotated 180 degrees, its closed side blocks reservoir opening 517, and it faces a door 503 in an isolating plate 502 disposed between the water of the water installation and the dispensing module. The warm vapor saturated pool water is prevented from condensing on the internal system components such as the dispenser by isolating plate 502. A motor actuated gear 515 rotates door 503, opening it briefly prior to discharging the powder. A stop prevents the motor actuated scoop from a runaway condition where the motor or the control system fails by preventing the scoop from continuous rotation that can discharge the entire reservoir into the water. This chemical dispensing module may be paired with a water quality dispensing module as described elsewhere herein.

The bottom 505 of the reservoir is sloped so that the powder will flow toward the dispenser's inlet 517 under gravity. Each pool water treatment powder such as calcium hypochlorite for chlorination or sodium hydroxide for pH adjustment will require a different sloped reservoir in order to ensure that even when the material is exposed to humidity or water for external sources or condensation, the reservoir is self-emptying. For example, when the reservoir contains calcium hypochlorite, an angle between 20 and 50 degrees (vertical being 0 degrees) enables self-emptying, but in order to optimize the reservoir volume for both granular and liquid reagents, an a reservoir bottom angle of 25 degrees may be used. Alternatively, a motor 520 with an offset weight 521 acting as a vibrator is attached to the bottom of the reservoir and is activated periodically in order to insure powder flow toward the dispenser's inlet.

Vents in the reservoir's outside protective enclosure channels ambient air above the isolation plate to ensure that condensation does not occur on the system's internal components.

Figure 6B:
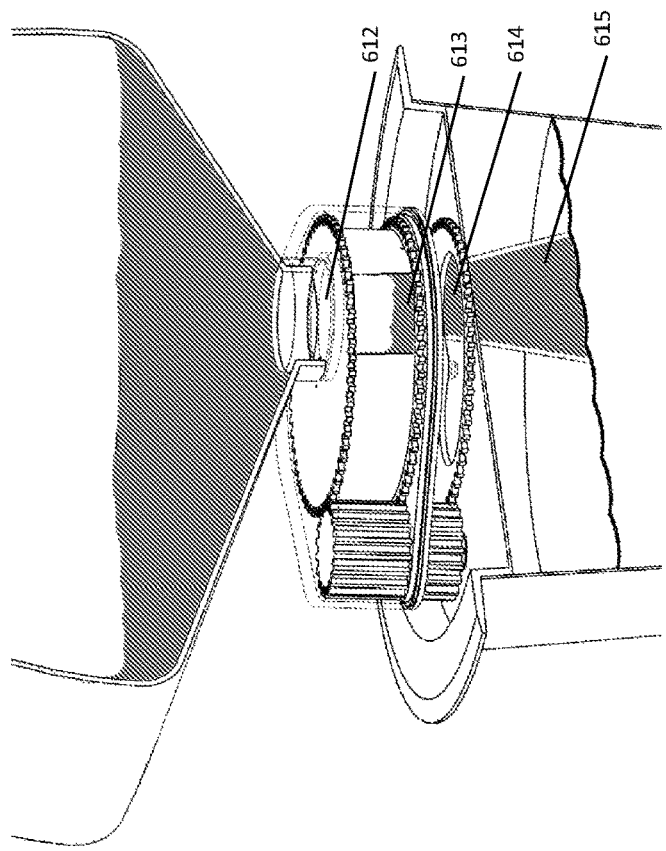
FIGS. 6A and 6B show a rotating gates powder reagent dispenser of a chemical dispensing module of a water quality management system for a water installation according to embodiments of the invention in the loading and dispensing positions respectively.
Figure 6A:
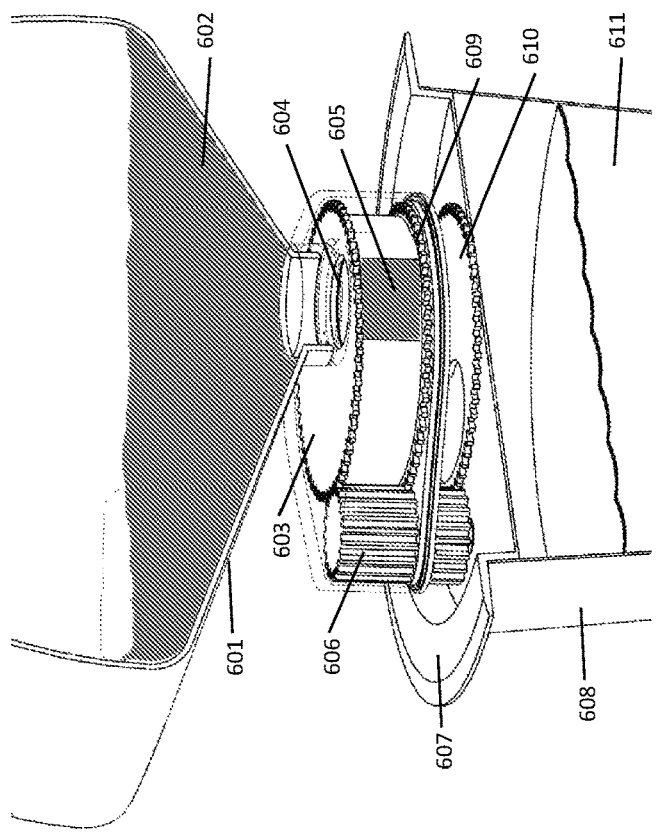

In another embodiment shown in FIGS. 6A and 6B, when the system's water quality measurement module indicates that chemicals need to be added to the water, the system's controller actuates a sliding plate 603 to gate the flow of powder 602 in reservoir 603 from flowing into measurement chamber 605. When the opening 604 of plate 603 is under the outlet of tank 601, the powder flows and fills chamber 605 but is stopped by the gate plate 609. As plates 603, 609 and 610 rotate further, as shown FIG. 6B, an opening 613 in plate 609 lines up with an opening 614 in the skimmer 608 and skimmer isolation plate 607, and the powder 615 is released into the water 611. At this position plate 603 seals the reservoir opening in position 612. A motor moving gears 606 insures that all three plates remain synchronized so that at no time powder can freely flow from the reservoir to the skimmer. The condensation on plate 610 can be vented so that at no time the powder encounters a moist surface and any humidity from the skimmer is blocked by the skimmer isolation plate and plate 610. This chemical dispensing module may be paired with a water quality dispensing module as described elsewhere herein.

Figure 7B:
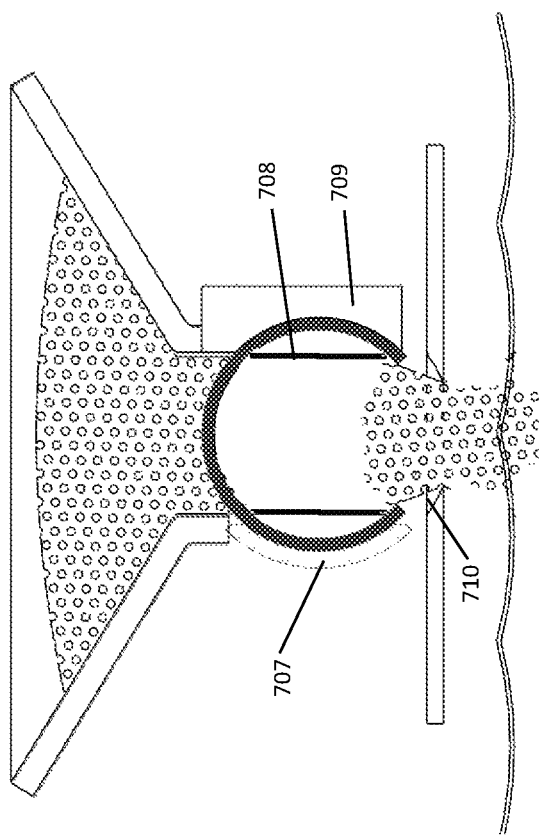
FIGS. 7A and 7B show a rotating cylinder powder reagent dispenser of a chemical dispensing module of a water quality management system for a water installation according to embodiments of the invention in the loading and dispensing positions respectively.
Figure 7A:
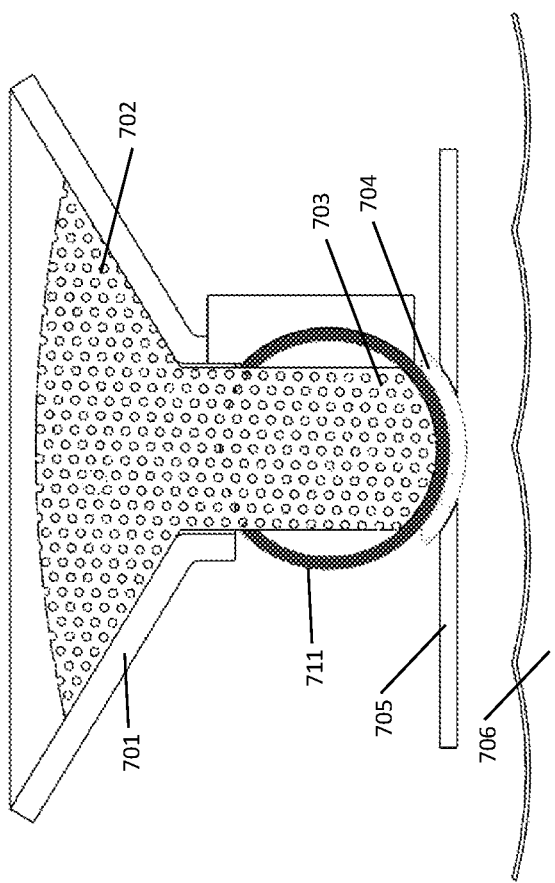

In another embodiment, FIGS. 7A and 7B describe a rotating thin cylindrical gate 711 made of appropriate material compatible with the powder such as a polymer or titanium When the system's water quality measurement module indicates that chemicals need to be added to the water, the system's controller rotates gate 711 from a storage position where its opening points sideways to the load position shown in FIG. 7A. The powder 702 from reservoir 701 flows into a cylindrical measurement chamber 708 and fills it as shown in 703. Door 704 closes the opening 710 in skimmer seal plate 705 to isolate it from the water 706. A gear motor rotates the gate 711 in block 709 180 degrees and rotates door 704 to position 707 so that the powder can flow through the opening in the skimmer isolation plate into the water. A pin in block 709 prevents the gate from rotating 360 degrees and prevents motor or control system failure from discharging uncontrollably the contents of the reservoir into the pool water. This chemical dispensing module may be paired with a water quality dispensing module as described elsewhere herein.

Figure 10:
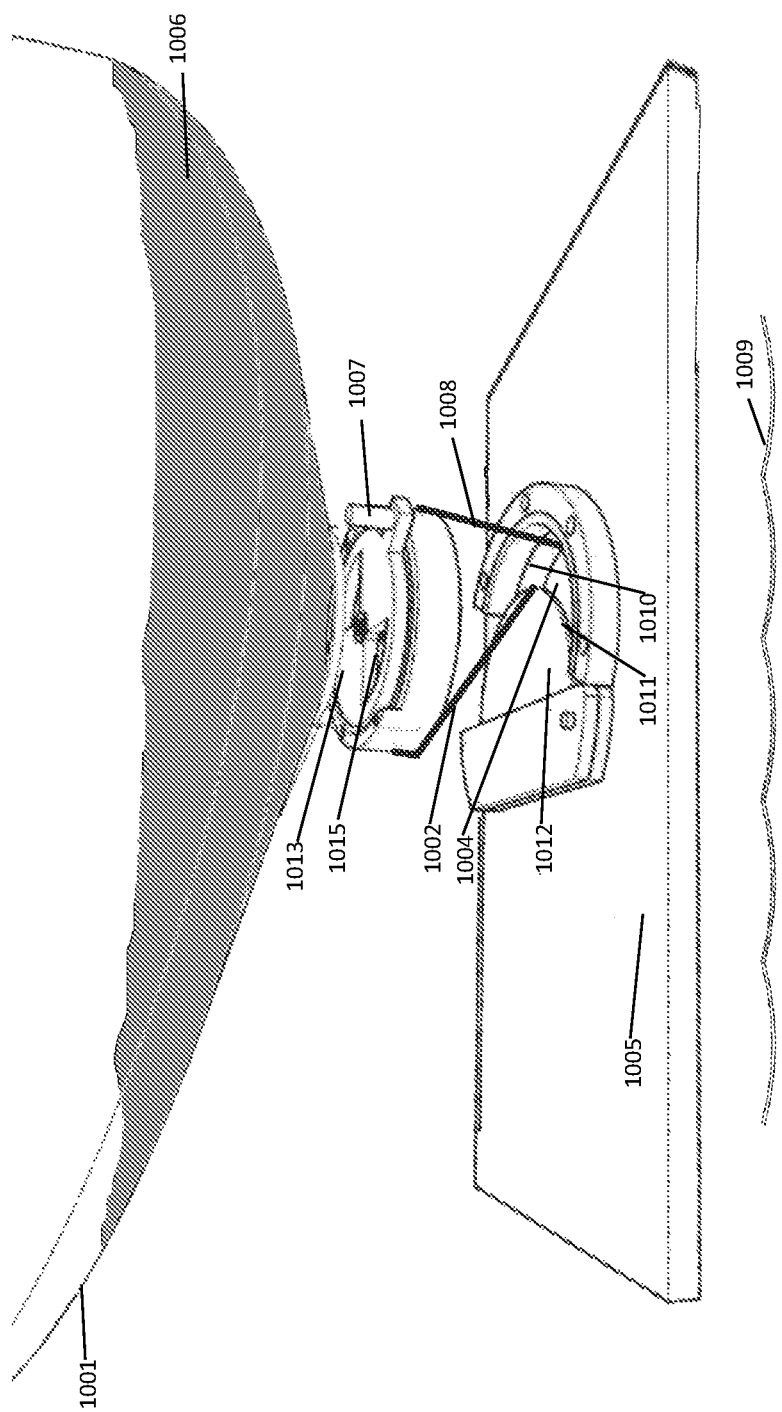
FIG. 10 shows a flexible tube based powder reagent dispenser of a chemical dispensing module of a water quality management system for a water installation according to embodiments of the invention.

In another embodiment, FIG. 10 describes a flexible tube based powder dispenser that shields the powder from ambient as well as pool water condensation. Powder 1006 in reservoir 1001 is gated by rotary or sliding gates forming a valve comprising a fixed plate 1013 with 90 degree holes 1015 and another similar plate above with a central hinge that can rotate 90 degrees via motor actuate lever 1007. When the openings line up, powder flows from the reservoir into the flexible tube whose fixed side wall 1008 is connected underneath the skimmer seal plate 1005 and whose movable opposite wall 1002 is connected underneath a rotating valve or door 1012. When the door is closed, the gate fills the tube with a predetermined volume of powder determined by the volume of the tube. When the gate is closed, the door is opened and the tube's content is emptied through opening 1004 into the water 1009. Any fines or particles that may cling to the tube will eventually fall through as powder is fed down or the tube is deformed by the opening and closing door. In the closed position, the door's leading edge 1011 pinches the tube against an elastomer 1010 to seal the entire mechanism from ambient and pool water humidity. This chemical dispensing module may be paired with a water quality dispensing module as described elsewhere herein.

Figure 11:
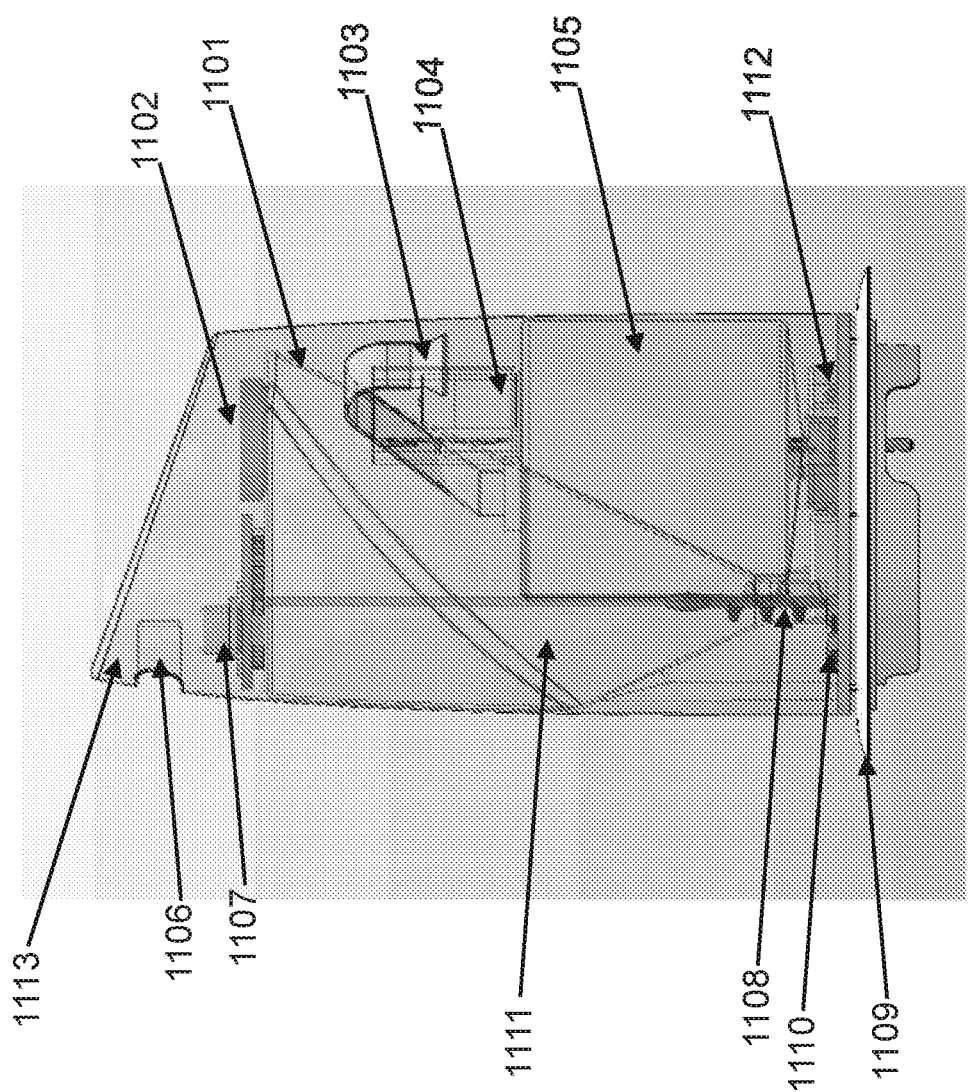
FIG. 11 shows yet another embodiment of a chemical dispensing module of a water quality management system for a water installation.

In another embodiment shown in FIG. 11, a powder dispensing tank with optimally sloping smooth walls 1111 (e.g., at an angle of 20-50 degrees, such as 25 degrees) and a wide fill port 1102 self-drains into a 1 inch diameter tube 1110 at the bottom of the sloped tank. An auger 1108 is disposed in and partially above the tube 1110 to engage and break up any clumps that may accumulate over time in the reservoir. The auger has a diameter just smaller than the inner diameter of the tube 1110. The auger has a pitch angle of 22 degrees which is less than the angle of repose for the powder so that it does not spontaneously flow through the auger. When the system's water quality measurement module indicates that chemicals need to be added to the water, the system's controller actuates motor 1107, which acts through gearbox and associated drive gear to spin the auger shaft, to dispense powder through tube. A door system or a tube pinch valve such as the one described above with respect to FIG. 10 or below with respect to FIG. 13 opens to allow for powder to flow through a hole in in baseplate 1109 into the skimmer or into the pool water. The reservoir can optionally have a bag inside which collapses as material is dispensed, and the entire reservoir and dispenser are submerged in the pool. The tube valve described above is pressurized with air to allow it to dispense the powder under water without allowing water to flow back into the reservoir. The auger system is able to break up clumps that may occur in the auger or above it as it actively pushes powder out with a flow rate controlled by the motor and associated battery-operated electronics 1104. A liquid reservoir 1105 wraps around the powder reservoir 1111 for optimal packaging, is filled via fill tube 1103 and dispenses through dispenser 1112 which are similar to those described above. A protective cover 1113 snaps onto the baseplate, and the entire unit can be lifted via a handle 1106 off the skimmer to allow access to the skimmer basket. The cover may also be removed from the reservoir by activating a release button to allow the user to fill the reservoirs while keeping children out of the chemical compartments. This chemical dispensing module may be paired with a water quality dispensing module as described elsewhere herein.

Figure 13:
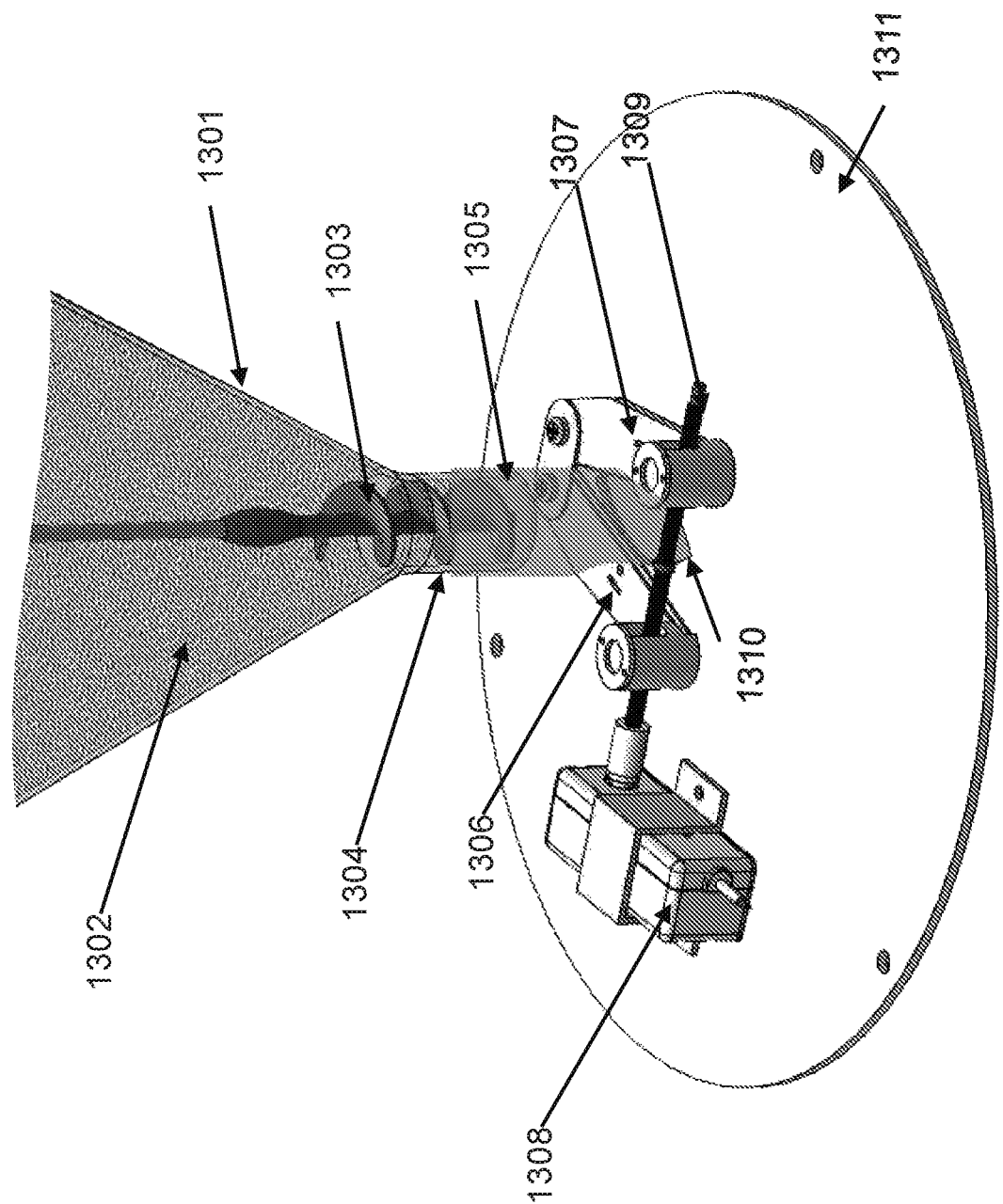
FIG. 13 shows still another embodiment of a chemical dispensing module of a water quality management system for a water installation.

FIG. 13 shows an optional feature that may be added to the embodiment shown in FIG. 11. A powder dispensing tank 1301 with optimally sloping smooth walls (e.g., at an angle of 20-50 degrees, such as 25 degrees) self-drains into a 1 inch diameter tube 1304 at the bottom of the sloped tank. An auger 1303 is disposed in and partially above the tube 1304 to engage and break up any clumps that may accumulate over time in the reservoir. The auger has a diameter just smaller than the inner diameter of the tube 1304. The auger has a pitch angle of 22 degrees which is less than the angle of repose for the powder so that it does not spontaneously flow through the auger. A motor 1107 spins the auger shaft to dispense powder through tube 1304. A flexible sleeve 1305 surrounds the outside of tube 1304 and extends through a discharge port 1310 in a plate 1311 covering, e.g., a skimmer of a water installation. A motor 1308, under the control of the system's controller and in coordination with the operation of the auger turns a screw 1309 to move pinchers 1306 and 1307 toward each other (to pinch sleeve 1305 closed) and away from each other (to allow sleeve 1305 to open to discharge powder received from tube 1304).

In some embodiments, pinchers 1306 and 1307 may have cooperating male and female surfaces to enhance the seal when the pinchers are closed. Pinching sleeve 1305 closed seals the system against water ingress. Movement of the sleeve during the pinching and unpinching operations also shakes loose any powder sticking to the interior wall of sleeve 1305.

The powder reservoirs may contain calcium hypochlorite, trichlor powder, lithium hypochlorite, or dichlor powder for water sanitation; sodium hydroxide, sodium carbonate, sodium bisulfate to adjust the pH; sodium bicarbonate to increase alkalinity; cyanuric acid to increase stabilizer.

The liquid reservoirs may contain sodium hypochlorite for water sanitation, hydrochloric acid or sodium hydroxide solution for pH control, sodium cyanurate slurry to increase stabilizer.

In yet another aspect of this invention, FIG. 8 describes a system whereby the user can fill the reservoirs without coming in contact with the chemicals. The reservoirs 804 and 805 are filled with a tube, 803 and 806 respectively, connected to the top of each reservoir. The distal end of each tube has a different size threaded hub, 802 and 807 respectively, to ensure that the user does not accidentally pour the wrong chemical into the reservoir. Hub 802 is tightened onto bottle 801, and the tube is pulled up to allow fluid gas exchange between the reservoir and the bottle. Similarly, hub 807 is screwed onto bag 808 with matching threaded fitment and a powder can flow to reservoir 805 without coming in contact with the user. The tubes can be made of suitable polymer so it can lay flat when stored in the unit.

Figure 9:
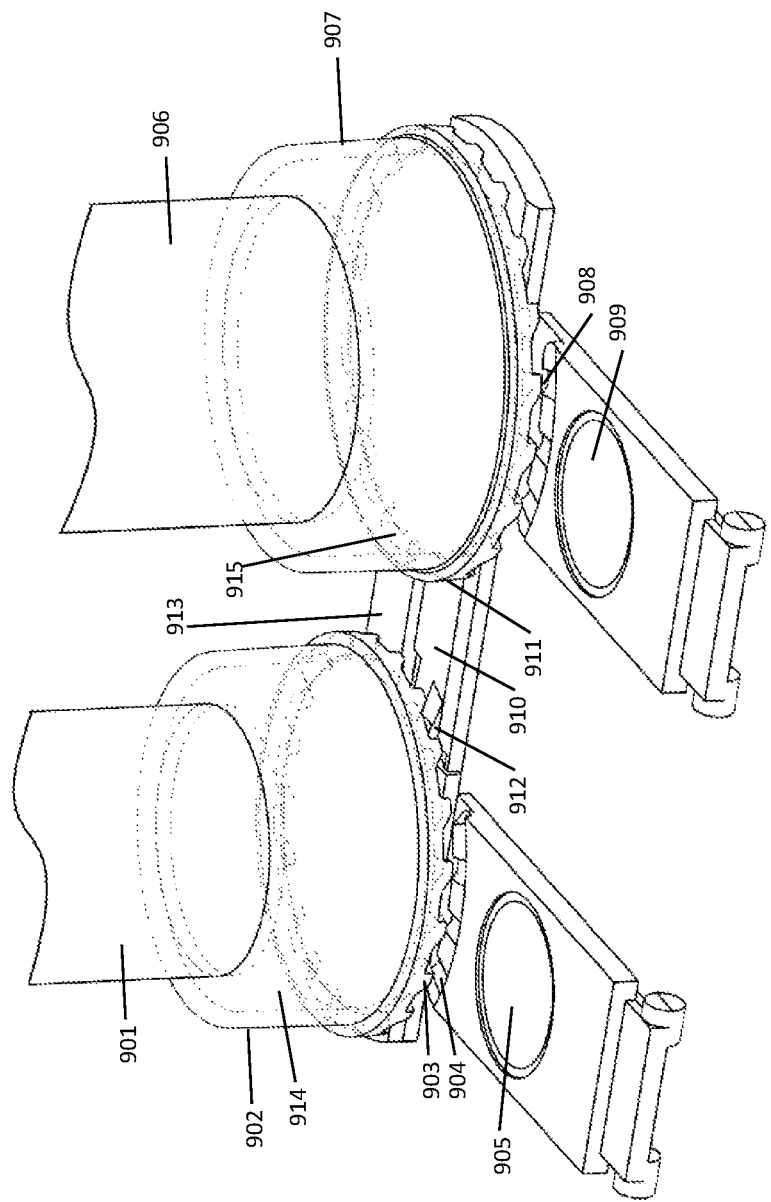
FIG. 9 shows a fill tube interlock mechanism of a chemical dispensing module of a water quality management system for a water installation according to embodiments of the invention.

In yet another aspect of this invention, in order to further insure that the user does not mix the chemicals that can result in violent reaction, release of chlorine gas, fire or other injury, a safety interlock is shown in FIG. 9. The screw on hub 902 rotates on a tube carrier that attaches to tube 901 and screws on a plug 914. The teeth 903 on the edge of the hub engage teeth 904 on a spring-loaded arm 905. When the arm is depressed by the user it acts as a child safety lock and allows the user to unscrew the hub and release the tube so it may be attached to the refill liquid bottle and the user can fill the reservoir as described above. A similar hub 907 with teeth interference 908 and child safety spring loaded lever 909 are used for the powder fill tube 906. But in order to prevent the user from accidentally pouring the wrong substance into the wrong reservoir, interlock spring loaded bars 910 and 913 prevent the user from removing a tube unless the other tube is connected to its hub. The powder hub 907 teeth when fully screwed on its plug depresses spring loaded interlock bar 910 at point 912. That pushes teeth 912 down and disengages them from the teeth of the liquid tube hub 902 and thus allows the user to unscrew it by depressing lever 905. However, if hub 907 is removed, the spring-loaded interlock bar 910 engages the teeth of hub 902 at location 912 and prevents the user from unscrewing it even if child safety bar 905 is depressed. A similar system is implemented with bar 913 whose teeth prevent hub 907 to be unscrewed if hub 902 is not in place at position 915.

It is desirable to monitor pool water chemistry for analytes that do not change quickly using laboratory grade analytics such as the SpinDisk system from LaMotte (Maryland, US) which are considerably more accurate than field analysis using test strips or liquid reagents. The state of analytes such as total hardness, copper, iron, cyanuric acid, phosphates, and salt affect the overall treatment of the pool water. Yet another aspect of the disclosure allows pool owners to cost effectively send a 3-10 milliliter sample of their pool water using inexpensive first class mail envelope.

Figure 12:
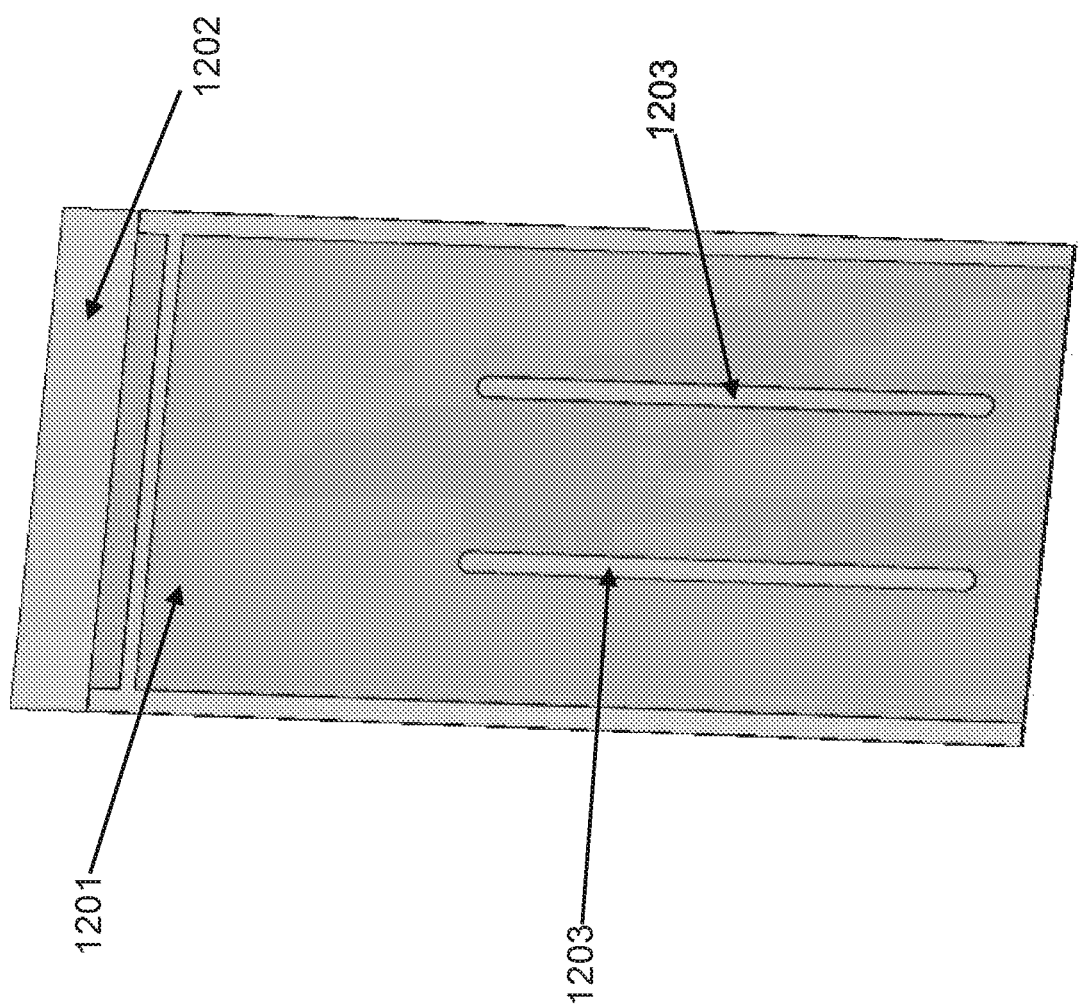
FIG. 12 shows a bag for mailing a sample of water from a water installation.

The bag, 1201, shown in FIG. 12, incorporates a zip lock 1202, and multiple pleats, 1203, to insure that the user can not over fill the bag when dipping it into the pool. The bag remains flat to comply with the USPO shipping regulations for first class envelopes of thickness and flexibility, and survives the belt pressure of postal sorting and stamping machines without spilling its content.

What is claimed is:

1. A water quality management system for a water installation containing water, the system comprising:
    a water quality measurement module adapted to monitor the water quality of the water in the water installation and to send water quality information to a controller; and
    a chemical dispensing module adapted to dispense at least one chemical directly into the water installation in response to signals from the controller based on a water quality measurement by the water quality measurement module, the chemical dispensing module comprising a reservoir adapted to contain the at least one chemical, a movable dispenser adapted and configured to advance a fixed quantity of the chemical out of the reservoir and through an opening on an exterior surface of the water quality management system into the water of the water installation in response to signals from the controller, the movable dispenser comprising an auger partially disposed in a tube extending to an exit port of the reservoir and partially disposed in the reservoir above the tube.

2. The system of claim 1 further comprising a flexible seal extending from the tube, the flexible seal having an open configuration in which chemical is permitted to flow from the tube into the water installation and a closed configuration in which the flexible seal seals the exit port of the reservoir.

3. The system of claim 2 further comprising an actuator moving the flexible seal from the open configuration to the closed configuration.

4. The system of claim 3 wherein the actuator comprises a pair of pinchers operated by a motor.

5. The system of claim 1 further comprising a motor adapted to actuate the auger.

6. The system of claim 5 wherein the motor is adapted to actuate the auger in response to signals from the controller based on a water quality measurement by the water quality measurement module.

7. The system of claim 1 wherein the water installation comprises a skimmer, the system further comprising a plate adapted to cover the skimmer of the water installation, the opening being disposed in the plate.

8. The system of claim 1 further comprising a liquid reagent reservoir and a dispenser communicating with the liquid reagent reservoir, the dispenser being adapted to dispense liquid reagent directly into the water installation through the openings in response to signals from the controller based on a water quality measurement by the water quality measurement module.

9. The system of claim 8 wherein the dispenser comprises a holding chamber in fluid communication with the liquid reagent reservoir and having a volume smaller than a volume of the liquid reagent reservoir.

10. The system of claim 9 wherein the dispenser further comprises a valve adapted to permit liquid reagent to flow from the liquid reagent reservoir into the holding chamber.

11. The system of claim 9 wherein the dispenser comprises an orifice configured to control a drip rate of liquid reagent from the holding chamber.

12. The system of claim 9 wherein the dispenser further comprises a nozzle adapted to deliver liquid reagent into water of the water installation.

13. The system of claim 8 wherein the liquid reagent is hydrochloric acid.

14. A water quality management system for a water installation containing water, the system comprising:
    a water quality measurement module adapted to monitor the water quality of the water in the water installation and to send water quality information to a controller; and
    a chemical dispensing module adapted to dispense a powdered chemical and a liquid reagent directly into the water installation through one or more openings in an exterior surface of the chemical dispensing module in response to signals from the controller based on a water quality measurement by the water quality measurement module,
    the chemical dispensing module comprising:
        a first reservoir adapted to contain the powdered chemical,
        a first dispenser adapted to dispense powdered chemical from the first reservoir through the one or more openings into the water installation,
        a second reservoir adapted to contain the liquid reagent, and
        a second dispenser comprising a holding chamber in fluid communication with the second reservoir and having a volume smaller than a volume of the liquid reagent reservoir, the second dispenser adapted to dispense liquid reagent from the holding chamber through the one or more openings into the water installation.

15. The system of claim 14 wherein the second dispenser further comprises a valve adapted to permit liquid reagent to flow from the second reservoir into the holding chamber.

16. The system of claim 14 wherein the second dispenser further comprises an orifice configured to control a drip rate of liquid reagent from the holding chamber.

17. The system of claim 14 wherein the second dispenser further comprises a nozzle adapted to deliver liquid reagent into water of the water installation.

18. The system of claim 14 wherein the liquid reagent is hydrochloric acid.

19. The system of claim 14 wherein the water installation comprises a skimmer, the system further comprising a plate adapted to cover the skimmer of the water installation, the one or more openings being disposed in the plate.

20. The system of claim 14 further comprising an auger adapted and configured to advance a fixed quantity of the powdered chemical out of the first reservoir and through the one or more openings into the water of the water installation in response to signals from the controller.

* * * * *